United States Patent
Fukuhori

(10) Patent No.: US 7,959,563 B2
(45) Date of Patent: Jun. 14, 2011

(54) CAPSULE ENDOSCOPE

(75) Inventor: Hitoshi Fukuhori, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 954 days.

(21) Appl. No.: 11/888,961

(22) Filed: Aug. 3, 2007

(65) Prior Publication Data

US 2008/0045798 A1 Feb. 21, 2008

(30) Foreign Application Priority Data

Aug. 21, 2006 (JP) ................. 2006-223792

(51) Int. Cl.
*A61B 1/06* (2006.01)
(52) U.S. Cl. ......... 600/175; 600/160; 600/176; 600/177
(58) Field of Classification Search .................. 600/101, 600/103, 160, 176–177
See application file for complete search history.

(56) References Cited

U.S. PATENT DOCUMENTS

| | | | |
|---|---|---|---|
| 5,547,457 A * | 8/1996 | Tsuyuki et al. ............... | 600/175 |
| 6,476,851 B1 | 11/2002 | Nakamura | |
| 2003/0227547 A1 | 12/2003 | Iddan | |
| 2005/0124858 A1 | 6/2005 | Matsuzawa et al. | |
| 2006/0170328 A1 * | 8/2006 | Kubota et al. ................. | 313/495 |
| 2008/0242935 A1 * | 10/2008 | Inoue ........................... | 600/176 |

FOREIGN PATENT DOCUMENTS

| | | |
|---|---|---|
| JP | 2001-231744 | 8/2001 |
| JP | 2005-080713 | 3/2005 |
| JP | 2005-080789 | 3/2005 |

* cited by examiner

*Primary Examiner* — Matthew J Kasztejna
(74) *Attorney, Agent, or Firm* — Kenyon & Kenyon LLP

(57) ABSTRACT

A capsule endoscope includes an objective lens and a transparent dome that covers the object side of the objective lens, and the transparent dome has negative refracting power. In the capsule endoscope of the present invention, the center of curvature of the object-side surface of the transparent dome disagrees with the center of curvature of the objective-lens-side surface of the transparent dome to satisfy the following condition:

$$Rb < L \leq Ra$$

where Ra is the radius of curvature of the object-side surface of the transparent dome, Rb is the radius of curvature of the objective-lens-side surface of the transparent dome, and L is a distance from the vertex of the object-side surface of the transparent dome to the most object-side surface of the objective lens.

5 Claims, 7 Drawing Sheets

$Rb < L \leq Ra$ $Rb < H < Ra$ $2Rc < Ra - Rb$

CAPSULE ENDOSCOPE

This application claims benefits of Japanese Application No. 2006-223792 filed in Japan on Aug. 21, 2006, the contents of which are incorporated herein by reference.

BACKGROUND OF THE INVENTION

1. Field of the Invention

This invention relates to a capsule endoscope that is swallowed in a body and thereby is capable of examining organs while moving inside the body.

2. Description of Related Art

In a capsule endoscope, its distal end is configured into a dome shape in view of fluidity in the body.

FIGS. 1A and 1B show a schematic structure of an example of the distal end of a conventional capsule endoscope.

In the capsule endoscope shown in FIGS. 1A and 1B, the object side of an objective lens 1 is covered with a transparent dome 2. Also, in FIGS. 1A and 1B, reference numeral 3 represents an image sensor and 4 represents light-emitting elements.

Capsule endoscopes in which the distal end is configured into the dome shape as mentioned above are set forth, for example, in Japanese Patent Kokai Nos. 2005-80789, 2001-231744, and 2005-80713.

SUMMARY OF THE INVENTION

The capsule endoscope according to the present invention includes an objective lens and a transparent dome that covers the object side of the objective lens. In this case, the transparent dome has negative refracting power.

In the capsule endoscope of the present invention, it is desirable that the center of curvature of the object-side surface of the transparent dome disagrees with the center of curvature of the objective-lens-side surface of the transparent dome to satisfy the following condition:

$$Rb < L \leq Ra \quad (1)$$

where Ra is the radius of curvature of the object-side surface of the transparent dome, Rb is the radius of curvature of the objective-lens-side surface of the transparent dome, and L is a distance from the vertex of the object-side surface of the transparent dome to the most object-side surface of the objective lens.

In the capsule endoscope of the present invention, it is desirable to satisfy the following condition:

$$T < Ra - Rb \quad (2)$$

where T is the center thickness of the transparent dome.

In the capsule endoscope of the present invention, it is desirable that the material of the transparent dome satisfies the following conditions:

$$\text{Moisture absorption rate} < 0.3\% \quad (3)$$

$$\text{Residual metals} < 1.5 \text{ ppm} \quad (4)$$

$$\text{Harder in pencil hardness than B} \quad (5)$$

In the capsule endoscope of the present invention, it is more desirable that the material of the transparent dome satisfies the following conditions:

$$\text{Moisture absorption rate} < 0.1\% \quad (6)$$

$$\text{Residual metals} < 0.5 \text{ ppm} \quad (7)$$

$$\text{Harder in pencil hardness than HB} \quad (8)$$

In the capsule endoscope of the present invention, it is desirable that light-emitting elements are arranged at positions opposite to the end face of the transparent dome to satisfy the following condition:

$$Rb < H < Ra \quad (9)$$

where H is a distance from the center axis of the transparent dome to the center of each of the light-emitting elements.

In the capsule endoscope of the present invention, it is desirable that a side opposite to the light-emitting elements, of the end face of the transparent dome, is configured as a curved surface to satisfy the following condition:

$$2Rc < Ra - Rb \quad (10)$$

where Rc is the radius of curvature of the side of the transparent dome opposite to the light-emitting elements.

In the capsule endoscope of the present invention, it is desirable that a reflecting plate satisfying the following condition with respect to wavelengths of 400-600 nm is provided on a plane on which the light-emitting elements are arranged:

$$\text{Reflectivity} > 90\% \quad (11)$$

In the capsule endoscope of the present invention, it is desirable that the light-emitting elements are LEDs.

According to the present invention, the capsule endoscope is obtained that the dead space of the dome occupying a large area in the conventional capsule endoscope is reduced, the overall length of the capsule endoscope is diminished, observation can be made in a wide field range, unwanted flare is minimized, a wide light distribution is possible, the screening property and safety can be improved, and the burden to the patient can be lessened.

These and other features and advantages of the present invention will become apparent from the following detailed description of the preferred embodiments when taken in conjunction with the accompanying drawings.

DETAILED DESCRIPTION OF THE PREFERRED EMBODIMENTS

Before undertaking the description of the embodiments, the function and effect of the present invention will be explained.

Figure 2A:
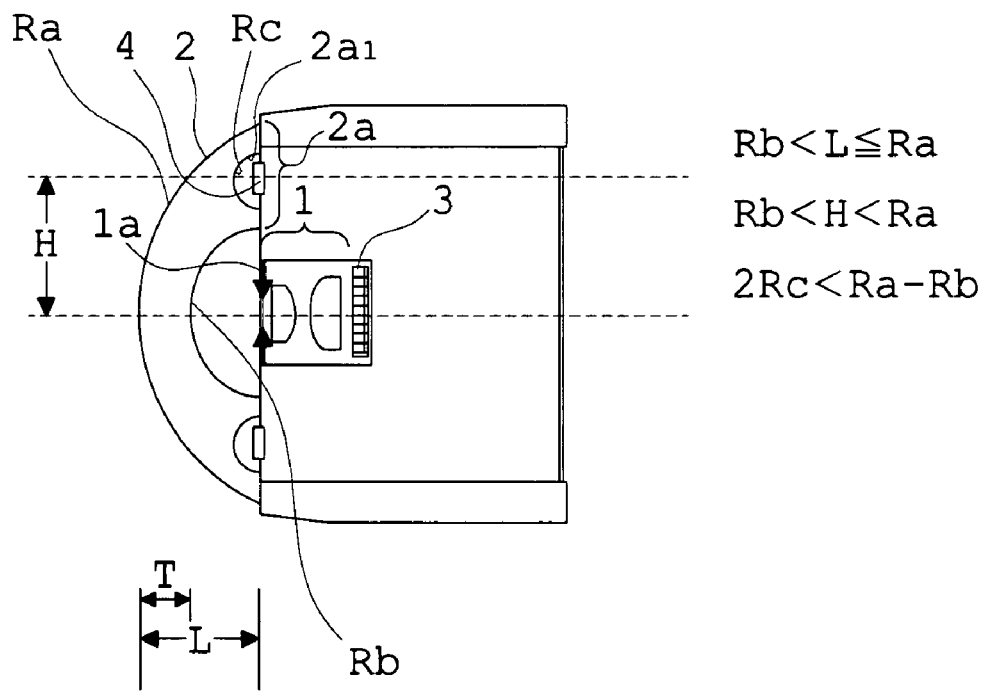
FIG. 2A is a sectional side view showing a schematic structure of the distal end, developed along the optical axis of an objective lens, of a capsule endoscope according to one embodiment of the present invention.
Figure 2B:
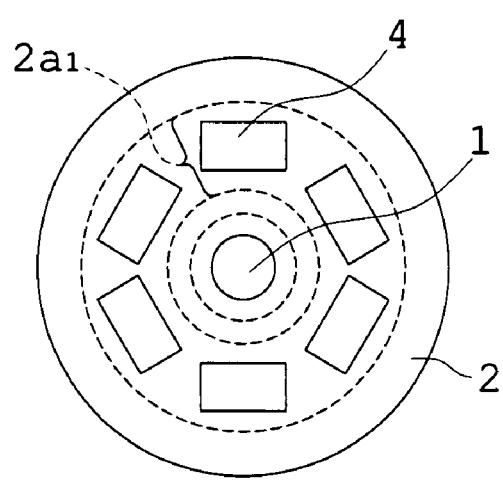
FIG. 2B is a front view showing the distal end of the capsule endoscope of FIG. 2A.
Figure 3A:
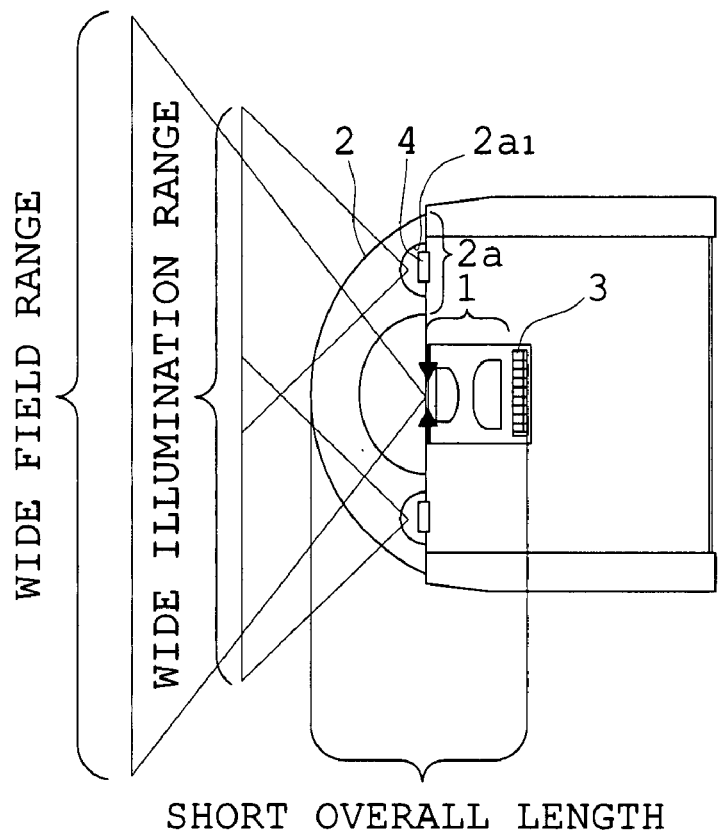
FIGS. 3A and 3B are explanatory views showing the function and effect of the capsule endoscope of the embodiment.
Figure 3B:
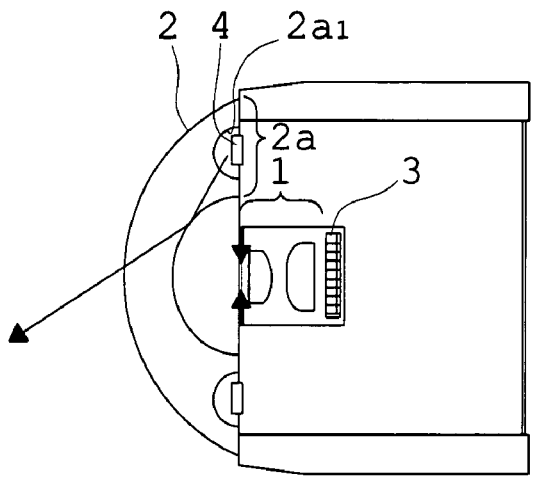
Figure 4:
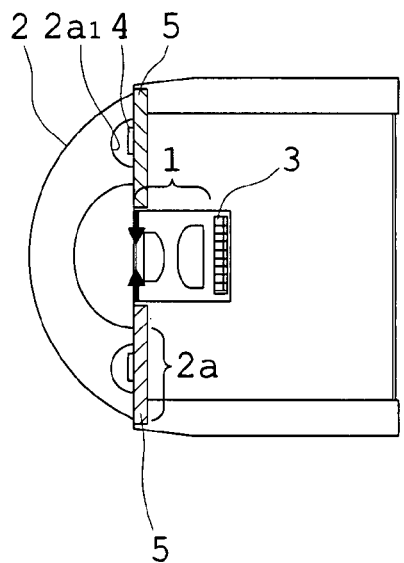
FIG. 4 is a sectional view showing a schematic structure of the distal end, developed along the optical axis of the objective lens, of the capsule endoscope according to one modified example of the embodiment.

FIGS. 2A and 2B show a schematic structure of the distal end of a capsule endoscope according to one embodiment of the present invention, and FIGS. 3A and 3B show the function and effect of the capsule endoscope of the embodiment. FIG. 4 shows a schematic structure of the distal end of the capsule endoscope according to one modified example of the embodiment.

The capsule endoscope of this embodiment has the objective lens 1 and the transparent dome 2. Also, in FIG. 2A, reference numeral 3 represents the image sensor. In the embodiment, one objective unit is constructed by combining the objective lens 1 with the image sensor 3.

The transparent dome 2 covers the object side of the objective lens 1.

Figure 1A:
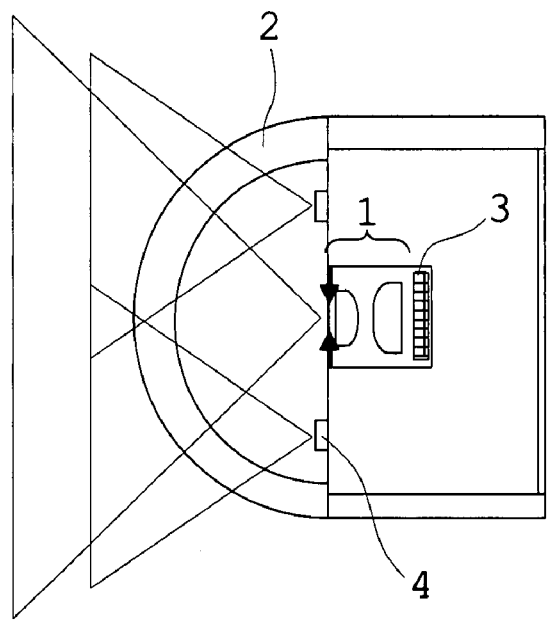
FIG. 1A is a sectional side view showing a schematic structure of an example of the distal end, developed along the optical axis of an objective lens, of a conventional capsule endoscope.
Figure 1B:
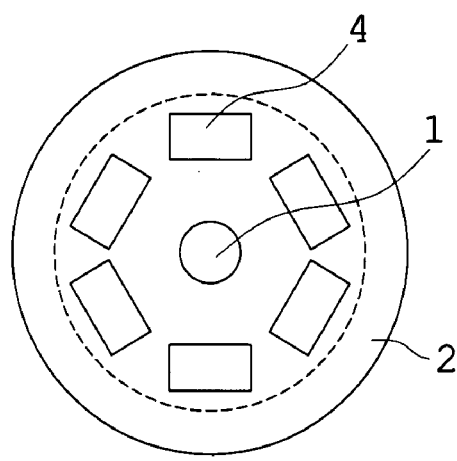
FIG. 1B is a front view showing the distal end of the capsule endoscope of FIG. 1A.

Here, the capsule endoscope of the embodiment, in contrast with the conventional capsule endoscope shown in FIGS. 1A and 1B, is such as to impart negative optical power to the transparent dome 2.

By doing so, as shown in FIG. 3A, the field angle of the capsule endoscope becomes wide, and as compared with the conventional capsule endoscope shown in FIGS. 1A and 1B, the field range can be extended without increasing the overall length of the capsule endoscope (for example, a distance from the vertex of the object-side surface of the transparent dome 2 to the image sensor 3) and the screening property can be improved.

In addition, it is also possible to shift the objective unit toward the top side of the transparent dome 2 while securing the field range equivalent to or wider than that of the conventional capsule endoscope. Whereby, the dead space in the transparent dome 2 can be reduced accordingly to diminish the overall length of the capsule endoscope. Moreover, the space of the capsule can be effectively utilized accordingly.

In the capsule endoscope of the embodiment, the center of curvature of the object-side surface of the transparent dome 2 disagrees with the center of curvature of the objective-lens-1-side surface of the transparent dome 2 to satisfy the following condition:

$$Rb < L \leq Ra \quad (1)$$

where Ra is the radius of curvature of the object-side surface of the transparent dome 2, Rb is the radius of curvature of the objective-lens-1-side surface of the transparent dome 2, and L is a distance from the vertex of the object-side surface of the transparent dome 2 to the most object-side surface of the objective lens 1 (the surface of a stop 1*a* in the embodiment).

The capsule endoscope of the embodiment satisfies the following condition:

$$T < Ra - Rb \quad (2)$$

where T is the center thickness of the transparent dome.

In the transparent dome 2, its material satisfies the following conditions:

$$\text{Moisture absorption rate} < 0.3\% \quad (3)$$

$$\text{Residual metals} < 1.5 \text{ ppm} \quad (4)$$

$$\text{Harder in pencil hardness than B} \quad (5)$$

In the transparent dome 2, it is more desirable that the material satisfies the following conditions:

$$\text{Moisture absorption rate} < 0.1\% \quad (6)$$

$$\text{Residual metals} < 0.5 \text{ ppm} \quad (7)$$

$$\text{Harder in pencil hardness than HB} \quad (8)$$

When the transparent dome 2 is constructed of such a material, the transparent dome 2 is hard to deform with respect to humidity, the degradation of optical performance can be kept to a minimum because of a small number of impurities, handling in product assembly is facilitated by the rugged transparent dome design, productivity is improved and a reduction of yield is suppressed, and greater safety for the human body is ensured.

In the capsule endoscope of the embodiment, unlike the conventional capsule endoscope, the light-emitting elements 4 (for example, LEDs) as light sources are arranged at positions opposite to an end face 2*a* of the transparent dome 2 to satisfy the following condition:

$$Rb < H < Ra \quad (9)$$

where H is a distance from the center axis of the transparent dome 2 to the center of each of the light-emitting elements 4.

By doing so, it is avoidable that illumination light from the light sources provided on the periphery of the objective lens 1 is reflected and scattered by the inner wall of the transparent dome 2 as shown in FIG. 3B. Unwanted light can thus be reduced.

In the capsule endoscope of the embodiment, a side $2a_1$ opposite to the positions where the light sources (the light-emitting elements 4) are arranged, of the end face 2*a* of the transparent dome, is configured as a curved surface (Rc) to satisfy the following condition:

$$2Rc < Ra - Rb \quad (10)$$

where Rc is the radius of curvature of the side $2a_1$ of the transparent dome 2 opposite to the light-emitting elements 4.

By doing so, as shown in FIG. 3A, wide light distribution becomes possible. Also, the radius of curvature of the Rc surface is changed and thereby the illumination range can be altered.

In the capsule endoscope of the embodiment, it is desirable that a reflecting plate 5, as shown in FIG. 4, satisfying the following condition with respect to wavelengths of 400-600 nm is provided on a plane on which the light-emitting elements 4 are arranged:

Reflectivity>90%  (11)

As mentioned above, when the reflecting plate 5 is provided at the position opposite to the end face 2a of the transparent dome 2, it becomes possible that illumination light repeating the total reflection inside the transparent dome 2 is efficiently transmitted toward the object side, and the illumination efficiency can be improved.

In accordance with the drawings, the embodiments of the present invention will be explained below.

Comparative Example 1

Figure 5:
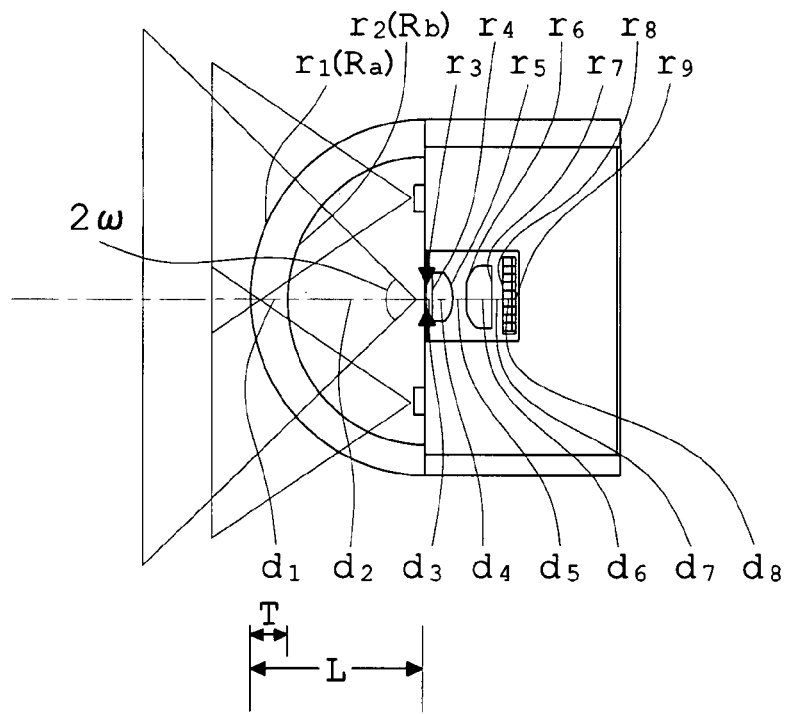
FIG. 5 is an explanatory view showing the optical arrangement, illumination range, and field angle, with a section developed along the optical axis, of the conventional capsule endoscope according to Comparative example 1 as opposed to Embodiments 1 and 2 of the present invention.

FIG. 5 shows the optical arrangement, illumination range, and field angle of the conventional capsule endoscope according to Comparative example 1 as opposed to Embodiments 1 and 2 of the present invention.

The fundamental optical arrangement of the capsule endoscope of Comparative example 1 is almost the same as in the conventional capsule endoscope shown in FIGS. 1A and 1B.

Numerical data of optical members constituting the capsule endoscope of Comparative example 1 are shown below. In the numerical data, $S_0$, $S_1$, ... denote surface numbers of optical members constituting the capsule endoscope; $r_1$, $r_2$, ... denote radii of curvature of optical members constituting the capsule endoscope; $d_1$, $d_2$, ... denote spacings between surfaces of the optical members; $n_{d1}$, $n_{d2}$, ... denote refractive indices of optical members constituting the capsule endoscope at the d line; $\nu_{d1}$, $\nu_{d2}$, ... denote Abbe's numbers of optical members constituting the capsule endoscope at the d line; and $2\omega$ denotes the total field angle. These symbols are also used for the numerical data of comparative examples and embodiments to be described later.

Numerical Data (Comparative Example 1)

$S_0$(object surface)  $r_0 = \infty$ $d_0 = 10.0000$ $S_1$  $r_1 = 5.9840$ $d_1 = 1.1968$  $n_{d1} = 1.58874$  $\nu_{d1} = 30.49$ $S_2$  $r_2 = 4.7872$ $d_2 = 4.7872$ $S_3$(stop)  $r_3 = \infty$ $d_3 = 0.0326$ $S_4$  $r_4 = \infty$ $d_4 = 0.9792$  $n_{d4} = 1.79196$  $\nu_{d4} = 47.37$ $S_5$  $r_5 = -1.3089$ $d_5 = 0.1088$ $S_6$  $r_6 = 1.8463$ $d_6 = 0.6746$  $n_{d6} = 1.79196$  $\nu_{d6} = 47.37$ $S_7$  $r_7 = \infty$ $d_7 = 0.3590$ $S_8$  $r_8 = \infty$ $d_8 = 0.4352$  $n_{d8} = 1.51825$  $\nu_{d8} = 64.14$ -continued $S_9$(imaging surface)  $r_9 = \infty$ $Ra = 5.984$ mm, $Rb = 4.7872$ mm, $L = 5.984$ mm $T = 1.1968$ mm $2\omega = 120°$ Embodiment 1

Figure 6:
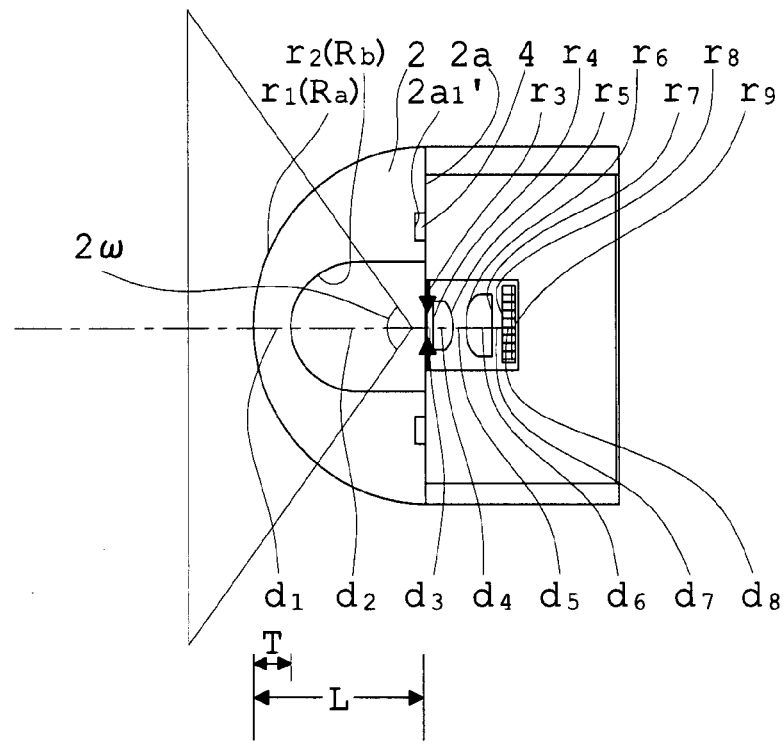
FIG. 6 is an explanatory view showing the optical arrangement and field angle, with a section developed along the optical axis, of the capsule endoscope according to Embodiment 1 of the present invention.

FIG. 6 shows the optical arrangement and field angle of the capsule endoscope according to Embodiment 1 of the present invention.

The fundamental optical arrangement of the capsule endoscope of Embodiment 1 is almost the same as in the capsule endoscope of the embodiment shown in FIGS. 2A and 2B. However, the end face 2a of the transparent dome 2 has a concave surface $2a_1'$ shaped to the contour of the light-emitting elements 4 so that the concave surface $2a_1'$ comes in close contact with the light-emitting elements 4.

The capsule endoscope of Embodiment 1 is the same in the overall length as the capsule endoscope of Comparative example 1, but it has a wider field range (field angle) due to the negative refracting power of the transparent dome 2 than that of Comparative example 1.

Subsequently, numerical data of optical members constituting the capsule endoscope of Embodiment 1 are shown below.

Numerical Data (Embodiment 1)

$S_0$(object surface)  $r_0 = \infty$ $d_0 = 10.0000$ $S_1$  $r_1 = 5.9840$ $d_1 = 1.1968$  $n_{d1} = 1.58874$  $\nu_{d1} = 30.49$ $S_2$  $r_2 = \underline{2.6000}$ $d_2 = 4.7872$ $S_3$(stop)  $r_3 = \infty$ $d_3 = 0.0326$ $S_4$  $r_4 = \infty$ $d_4 = 0.9792$  $n_{d4} = 1.79196$  $\nu_{d4} = 47.37$ $S_5$  $r_5 = -1.3089$ $d_5 = 0.1088$ $S_6$  $r_6 = 1.8463$ $d_6 = 0.6746$  $n_{d6} = 1.79196$  $\nu_{d6} = 47.37$ $S_7$  $r_7 = \infty$ $d_7 = 0.3590$ $S_8$  $r_8 = \infty$ $d_8 = 0.4352$  $n_{d8} = 1.51825$  $\nu_{d8} = 64.14$ $S_9$(imaging surface)  $r_9 = \infty$ $Ra = 5.984$ mm, $Rb = 2.6$ mm, $L = 5.984$ mm $T = 1.1968$ mm $2\omega = 170°$

Embodiment 2

Figure 7:
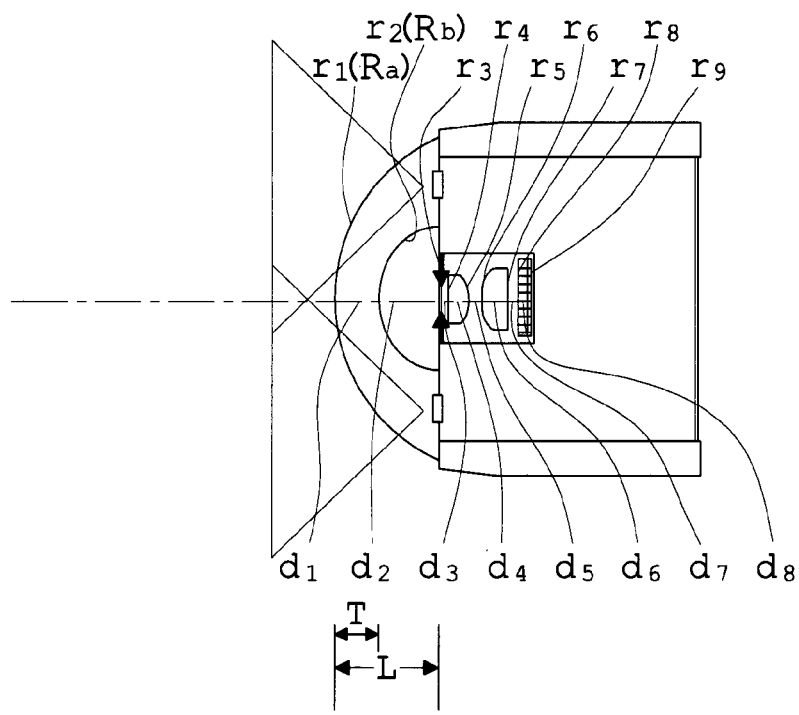
FIG. 7 is an explanatory view showing the optical arrangement and field angle, with a section developed along the optical axis, of the capsule endoscope according to Embodiment 2 of the present invention.

FIG. 7 shows the optical arrangement and field angle of the capsule endoscope according to Embodiment 2 of the present invention.

The fundamental optical arrangement of the capsule endoscope of Embodiment 2 is almost the same as in the capsule endoscope of the embodiment shown in FIGS. 2A and 2B.

The capsule endoscope of Embodiment 2 has a wider field range (field angle) due to the negative refracting power of the transparent dome 2 than that of Comparative example 1 and at the same time, is reduced in the overall length.

Subsequently, numerical data of optical members constituting the capsule endoscope of Embodiment 2 are shown below.

Numerical Data (Embodiment 2)

$S_0$(object surface)   $r_0 = \infty$ $d_0 = 10.0000$ $S_1$   $r_1 = 5.9840$ $d_1 = 1.1968$   $n_{d1} = 1.58874$   $\nu_{d1} = 30.49$ $S_2$   $r_2 = \underline{1.5000}$ $d_2 = \underline{1.5000}$ $S_3$(stop)   $r_3 = \infty$ $d_3 = 0.0326$ $S_4$   $r_4 = \infty$ $d_4 = 0.9792$   $n_{d4} = 1.79196$   $\nu_{d4} = 47.37$ $S_5$   $r_5 = -1.3089$ $d_5 = 0.1088$ $S_6$   $r_6 = 1.8463$ $d_6 = 0.6746$   $n_{d6} = 1.79196$   $\nu_{d6} = 47.37$ $S_7$   $r_7 = \infty$ $d_7 = 0.3590$ $S_8$   $r_8 = \infty$ $d_8 = 0.4352$   $n_{d8} = 1.51825$   $\nu_{d8} = 64.14$ $S_9$(imaging surface)   $r_9 = \infty$ $Ra = 5.984$ mm, $Rb = 1.5$ mm, $L = 2.6968$ mm $T = 1.1968$ mm $2\omega = 160°$

Embodiment 3

In the capsule endoscope of Embodiment 3, the transparent dome 2 in the capsule endoscope of each of Embodiments 1 and 2 is constructed of the following material:

Polycarbonate resin: lupilon H3000 (Mitsubishi Engineering-Plastics Corporation)

Moisture absorption rate: 0.15% or less

Residual metals: 1.36 ppm

Pencil hardness: HB

Embodiment 4

In the capsule endoscope of Embodiment 4, the transparent dome 2 in the capsule endoscope of each of Embodiments 1 and 2 is constructed of the following material:

Cycloolefin polymer: ZEONEX 330R (ZEON CORPORATION)

Moisture absorption rate: 0.01% or less

Residual metals: 0.06 ppm

Pencil hardness: 3H

Alternatively, the transparent dome 2 may be constructed of the following material:

ZEONEX 480R, ZEONEX E48R, ZEONEX 480

Moisture absorption rate: 0.01% or less

Residual metals: 0.06 ppm

Pencil hardness: H

Embodiment 5

Figure 8:
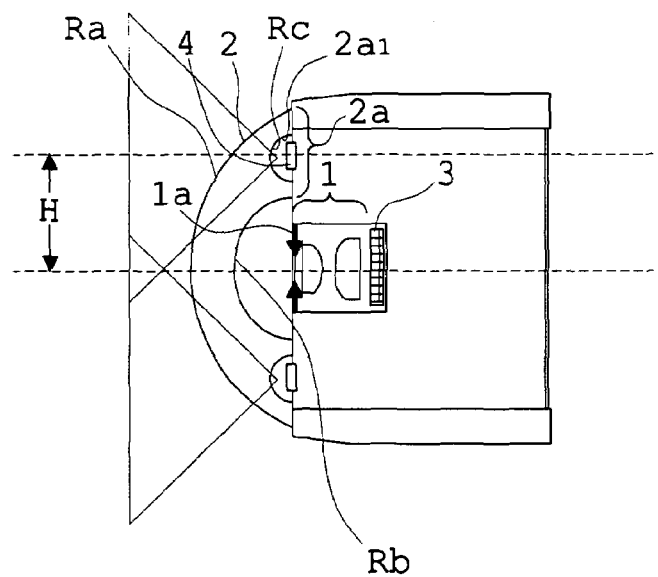
FIG. 8 is an explanatory view showing the optical arrangement and illumination range, with a section developed along the optical axis, of the capsule endoscope according to Embodiment 5 of the present invention.
Figure 9:
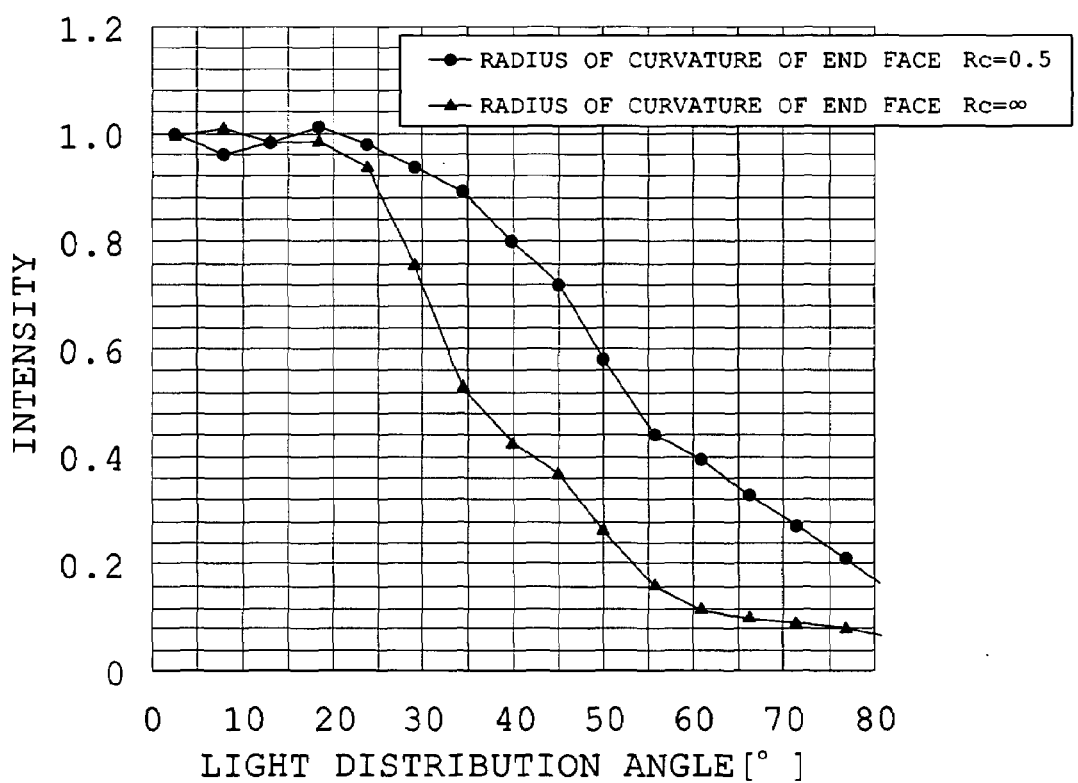
FIG. 9 is a graph showing the light intensity plotted against the light distribution angle in the capsule endoscope using the transparent dome according to Embodiment 5 in which the side opposite to the light-emitting elements is configured as a curved surface in comparison with the case where it is not provided with the curved surface.

FIG. 8 shows the optical arrangement and illumination range of the capsule endoscope according to Embodiment 5 of the present invention. FIG. 9 is a graph showing the light intensity plotted against the light distribution angle in the capsule endoscope using the transparent dome according to Embodiment 5 in which the side opposite to the light-emitting elements is configured as a curved surface in comparison with the case where it is not provided with the curved surface.

The fundamental optical arrangement of the capsule endoscope of Embodiment 5 is nearly the same as in the capsule endoscope of the embodiment shown in FIGS. 2A and 2B or Embodiment 2 shown in FIG. 7, and the side $2a_1$ opposite to the light-emitting elements 4, of the end face 2a of the transparent dome 2, is configured as the curved surface.

In the capsule endoscope of Embodiment 5, the radius of curvature Ra of the object-side surface of the transparent dome 2 is 5.5 mm; the radius of curvature Rb of the objective-lens-1-side surface of the transparent dome 2 is 2.3 mm; the radius of curvature Rc of the side of the transparent dome 2 opposite to the light-emitting elements 4 is 0.5 mm; and the distance H from the center axis of the transparent dome 2 to the center of each of the light-emitting elements 4 is 3.3 mm.

Comparative Example 2

As the comparative example of the capsule endoscope of Embodiment 5, the capsule endoscope is used which has the same structure as Embodiment 5 with the exception that the end face 2a of the transparent dome 2 has the concave surface $2a_1'$ shaped to the contour of the light-emitting elements 4 so that the concave surface $2a_1'$ comes in close contact with the light-emitting elements 4 (Rc=∞).

In each of the capsule endoscopes of Embodiment 5 and Comparative example 2, the light intensity relative to the light distribution angle is studied.

As a result, according to the capsule endoscope using the transparent dome 2 in which the side $2a_1$ opposite to the light-emitting elements 4 is configured as the curved surface, as depicted in FIG. 9, the light distribution is wider than in the case where the end face 2a is not provided with the curved surface.

Embodiment 6

Figure 10:
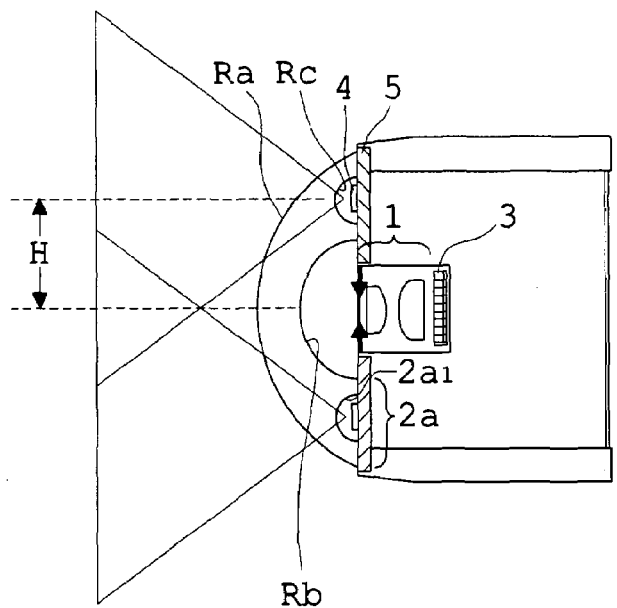
FIG. 10 is an explanatory view showing the optical arrangement and illumination range, with a section developed along the optical axis, of the capsule endoscope according to Embodiment 6 of the present invention.
Figure 11:
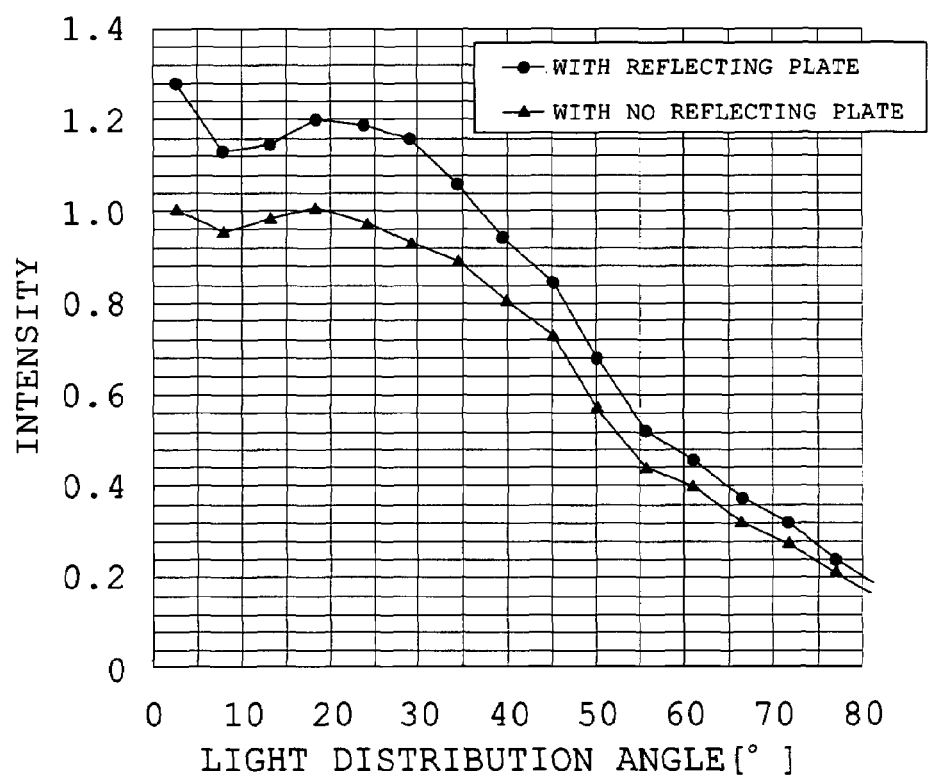
FIG. 11 is a graph showing the light intensity plotted against the light distribution angle in the capsule endoscope according to Embodiment 6 in which the reflecting plate whose reflectivity exceeds 90% with respect to wavelengths of 400-600 nm is provided on the plane on which the light-emitting elements are arranged, in comparison with the case where the reflecting plate is not provided.

FIG. 10 shows the optical arrangement and the illumination range of the capsule endoscope according to Embodiment 6 of the present invention. FIG. 11 is a graph showing the light intensity plotted against the light distribution angle in the capsule endoscope according to Embodiment 6 in which the reflecting plate whose reflectivity exceeds 90% with respect to wavelengths of 400-600 nm is provided on the plane on which the light-emitting elements are arranged, in comparison with the case where the reflecting plate is not provided.

The fundamental optical arrangement of the capsule endoscope of Embodiment 6 is nearly the same as in the capsule endoscope according to the modified example shown in FIG. 4, and the reflecting plate 5 whose reflectivity exceeds 90% with respect to wavelengths of 400-600 nm is provided on the plane on which the light-emitting elements are arranged.

In the capsule endoscope of Embodiment 6, the radius of curvature Ra of the object-side surface of the transparent dome 2 is 5.5 mm; the radius of curvature Rb of the objective-lens-1-side surface of the transparent dome 2 is 2.3 mm; the radius of curvature Rc of the side of the transparent dome 2 opposite to the light-emitting elements 4 is 0.5 mm; and the distance H from the center axis of the transparent dome 2 to the center of each of the light-emitting elements 4 is 3.3 mm.

Comparative Example 3

As the comparative example of the capsule endoscope of Embodiment 6, the capsule endoscope is used which has the same structure as Embodiment 6 with the exception that the reflecting plate 5 is not provided on the plane on which the light-emitting elements 4 are arranged.

In each of the capsule endoscopes of Embodiment 6 and Comparative example 3, the light intensity relative to the light distribution angle is studied.

As a result, according to the capsule endoscope in which the reflecting plate 5 whose reflectivity exceeds 90% with respect to wavelengths of 400-600 nm is provided on the plane on which the light-emitting elements 4 are arranged, as depicted in FIG. 11, the light intensity is increased at the same light distribution angle and the illumination efficiency is improved, as compared with the case where the reflecting plate is not provided.

The capsule endoscope of the present invention is useful in the field of medicine in which the burden to the patient is lessened as far as possible and at the same time, a high-accuracy diagnosis of the digestive tract is needed.

What is claimed is:
1. A capsule endoscope comprising:
an objective lens;
light-emitting elements; and
a transparent dome that covers an object side of both of the objective lens and the light-emitting elements and is arranged on a most object side in the capsule endoscope,
wherein the transparent dome has negative refracting power, and
wherein a center of curvature of an object-side surface, which is an outside surface, of the transparent dome disagrees with a center of curvature of an objective-lens-side surface, which is an inside surface facing the objective lens, of the transparent dome, to satisfy the following condition:

$$Rb < L \leq Ra$$

where Ra is a radius of curvature of the object-side surface of the transparent dome, Rb is a radius of curvature of the objective-lens-side surface of the transparent dome, and L is a distance from a vertex of the object-side surface of the transparent dome to a most object-side surface of the objective lens.

2. A capsule endoscope according to claim 1, further satisfying the following condition:

$$T < Ra - Rb$$

where T is a center thickness of the transparent dome.

3. A capsule endoscope according to claim 1, wherein the light-emitting elements are arranged at positions within a zone between an edge of the object-side surface of the transparent dome and an edge of the objective-lens-side surface of the transparent dome, to satisfy the following condition:

$$Rb < H < Ra$$

where H is a distance from a center axis of the transparent dome to a center of each of the light-emitting elements.

4. A capsule endoscope according to claim 3, wherein the transparent dome has, in a portion between the edge of the object-side surface and the edge of the objective-lens-side surface, a curved surface that forms a concavity to accommodate the light-emitting elements and satisfies the following condition:

$$2Rc < Ra - Rb$$

where Rc is a radius of curvature, in a plane containing the center axis of the transparent dome, of the curved surface that forms the concavity.

5. A capsule endoscope according to claim 3, wherein a reflecting plate satisfying the following condition with respect to wavelengths of 400-600 nm is provided on a plane on which the light-emitting elements are arranged:
Reflectivity >90%.

* * * * *